(12) United States Patent
Pasquet et al.

(10) Patent No.: US 8,092,497 B2
(45) Date of Patent: Jan. 10, 2012

(54) INTERVERTEBRAL IMPLANT FOR THE LUMBOSACRAL JOINT

(75) Inventors: Denis Pasquet, Quinsac (FR); Régis Le Couëdic, Andresy (FR); Jacques Senegas, Merignac (FR)

(73) Assignee: Zimmer Spine S.A.S., Bordeaux (FR)

( * ) Notice: Subject to any disclaimer, the term of this patent is extended or adjusted under 35 U.S.C. 154(b) by 742 days.

(21) Appl. No.: 12/064,935

(22) PCT Filed: Aug. 25, 2006

(86) PCT No.: PCT/FR2006/050811
§ 371 (c)(1),
(2), (4) Date: Aug. 29, 2008

(87) PCT Pub. No.: WO2007/023240
PCT Pub. Date: Mar. 1, 2007

(65) Prior Publication Data
US 2009/0018662 A1    Jan. 15, 2009

(30) Foreign Application Priority Data
Aug. 26, 2005    (FR) ..................... 05 08767

(51) Int. Cl.
*A61B 17/70* (2006.01)
(52) U.S. Cl. ....................................... 606/248
(58) Field of Classification Search ........... 606/246–279
See application file for complete search history.

(56) References Cited

U.S. PATENT DOCUMENTS
2004/0117017 A1    6/2004  Pasquet et al.
2006/0271044 A1*   11/2006 Petrini et al. ............... 606/61
2006/0282078 A1*   12/2006 Labrom et al. ............. 606/61
2007/0203491 A1*    8/2007 Pasquet et al. ............. 606/61

FOREIGN PATENT DOCUMENTS
EP    1138268    10/2001
FR    2858929     2/2005

OTHER PUBLICATIONS

International Search Report and Written Opinion for PCT/FR2006/050811, completed Feb. 5, 2007, mailed Feb. 16, 2007, 9 pgs.
English Translation of the Written Opinion for PCT/FR2006/050811, completed Feb. 5, 2007, mailed Feb. 16, 2007, 4 pgs.
French Preliminary Search Report for FR0508767 completed May 29, 2006, 2 pgs.
International Preliminary Examination Report for PCT/FR2006/050811, issued on Feb. 26, 2008, 6 pgs.
English translation of the International Preliminary Examination Report for PCT/FR2006/050811, issued on Feb. 26, 2008, 6 pgs.

\* cited by examiner

*Primary Examiner* — Eduardo C Robert
*Assistant Examiner* — Summer Kostelnik
(74) *Attorney, Agent, or Firm* — Sprinkle IP Law Group

(57) ABSTRACT

The invention provides an intervertebral implant for the lumbo-sacral joint, the implant comprising a spacer suitable for being disposed between the fifth lumbar vertebra L5 and the vertebra S1 of the sacrum that is articulated to the vertebra L5. The implant comprises a flexible tie having end portions suitable for being fastened to the sacrum with the help of fasteners such as pedicular screws. The flexible tie has an intermediate portion suitable for co-operating with a connection system such as a hook provided on the spacer so that the flexible tie connects the spacer to the sacrum. The flexible tie is put under tension in such a manner as to exert a return force on the spacer towards the vertebra S1.

18 Claims, 5 Drawing Sheets

INTERVERTEBRAL IMPLANT FOR THE LUMBOSACRAL JOINT

CROSS-REFERENCE TO RELATED APPLICATIONS

This is a national stage application of International Application No. PCT/FR2006/050811, filed Aug. 25, 2006, which claims priority to French Application No. FR 0508767, filed Aug. 26, 2005. Both applications are fully incorporated by reference herein.

TECHNICAL FIELD

The present invention relates to an intervertebral implant for the lumbo-sacral joint, the implant comprising a spacer suitable for being placed between the fifth lumbar vertebra and the vertebra of the sacrum that is articulated thereto.

BACKGROUND OF THE RELATED ART

In the anatomy of the spine, as shown in FIG. 1, the sacrum is situated beneath the lumbar vertebrae and is made up of five vertebrae written S1 to S5 which, over the course of human evolution, have become fused to one another. Nowadays, four pairs of holes, referred to as intervertebral foramens 11, remain between the sacral vertebrae S1 to S5. These holes, distributed on either side of the sagittal plane of the spine constitute traces of the epoch when these vertebrae were separate.

The top vertebra of the sacrum, written S1, is articulated to the fifth lumbar vertebra, written L5, as shown in FIG. 1. This joint constitutes the lumbo-sacral joint, or the L5-S1 joint.

Furthermore, each lumbar vertebra presents a middle posterior projection known as the spinous process 10, sometimes referred to below as the process. The sacral vertebrae have lost their spinous processes during evolution, and instead they merely conserve respective small residual bumps 12.

SUMMARY OF THE DISCLOSURE

In man, some kinds of back pain are associated with stresses acting on the intervertebral disk situated between the vertebrae L5 and S1, which stresses are themselves associated with the vertebrae L5 and S1 moving relative to each other, in particular during extension and flexion of the spine.

Intervertebral implants are already known that seek to limit the displacement of the vertebrae L5 and S1 relative to each other in order to provide relief for the intervertebral disk, and in particular one such implant is described in document FR 2 858 929.

That implant is a spacer presenting a top face and an opposite bottom face, a groove being formed in the top face for receiving the spinous process of the vertebra L5, and a longitudinal housing orthogonal to said groove being formed in the bottom face for directly receiving the top portion or posterior arc of the vertebra S1.

That implant further comprises two straps that are secured to said spacer, in such a manner that the first strap is suitable for being tightened around the process of the vertebra L5 in order to hold it in said groove, and the second strap is passed through an opening made in the sacrum and is suitable for being tightened so as to hold the spacer against the vertebra S1.

That type of implant leads to two types of problem: in order to be put into place, it requires an opening to be made in the sacrum, and in operation, the second strap rubs against the sacrum.

The present invention seeks to solve those problems.

For this purpose, the invention provides an intervertebral implant for the lumbo-sacral joint, the implant comprising a spacer suitable for being placed between the fifth lumbar vertebra L5 and the vertebra S1 of the sacrum that is articulated to the vertebra L5, the implant being characterized in that it includes a flexible tie having end portions that can be fastened to the sacrum with the help of fasteners, the flexible tie presenting an intermediate portion suitable for co-operating with a connection system provided on said spacer in such a manner that the flexible tie connects the spacer to the sacrum.

By means of the flexible tie, the spacing between the spacer and the vertebra S1 is limited. Preferably, it is desirable to avoid any separation of the spacer relative to the vertebra S1 so as to minimize the freedom of movement between the vertebrae L5 and S1 during flexing of the spine. This object is achieved by acting on the length and/or the tension of the flexible tie when it is elastic.

Advantageously, the flexible tie is put under tension so as to exert a return force on the spacer towards the vertebra S1, thus enabling the spacer to be pressed against said vertebra. In a first example, in order to enable the flexible tie to be put under tension, the end portions of the tie are movable relative to said fasteners and can be pulled away from said spacer so as to put the flexible tie under tension, prior to being prevented from moving relative to the fasteners. In that example, the flexible tie is not necessarily elastically deformable, and advantageously it is capable of sliding inside a recess formed in said fasteners (so as to be guided when traction is applied to its ends). In a second example, the end portions of the tie are not movable relative to said fasteners, and the flexible tie is elastically deformable, its length being such that it is under tension when it co-operates with the connection system of the spacer and when the fasteners are in position on the sacrum.

In a first embodiment of the invention, said fasteners comprise pedicular screws that are suitable for being anchored in the sacrum, each presenting a screw head fitted with a fastening system, each end portion of the flexible tie being fastened to said screw head with the help of said fastening system.

The fastening system used must be capable of being manipulated easily by the surgeon, since while performing the operation, the work space available in the lumbo-sacral region is small and visibility can be poor, in particular because of blood.

Advantageously, said fastening system comprises a body portion presenting a recess suitable for receiving an end portion of said flexible tie and a clamping screw for clamping the flexible tie inside said recess.

The recess and clamping screw solution constitutes a structure that is simple and easily manipulated. The term "recess" is used to designate any suitable type of empty space. It may be constituted by a blind hole, a through hole, a groove, .... The clamping screw is movable relative to the recess and enables the flexible tie to be fastened by being clamped inside the recess.

In a first example of an implant according to the abovementioned first embodiment, the screw head of each pedicular screw forms said body portion of the fastening system.

In a second example of an implant according to the abovementioned first embodiment, said body portion is extended by a rod, the screw heads of the pedicular screws each presenting a respective recess suitable for receiving said rod and a clamping screw for fastening said rod inside said recess.

This second example, of structure that is more complex than the first, provides the option of moving the body portion of the fastening system relative to the screw head. This enables each body portion and its recess to be oriented in a preferred direction and/or makes it possible to adjust the tension in the flexible tie after it has been fastened inside the recesses of the body portions and connected to the spacer.

In a second embodiment of the invention, said fasteners comprise hooks suitable for being hooked in the intervertebral foramens of the sacrum, each end portion of the flexible tie being fastened to a said hook.

BRIEF DESCRIPTION OF THE DRAWINGS

The invention and its advantages can be better understood on reading the following detailed description. The description makes reference to the accompanying figures, in which.

DETAILED DESCRIPTION

Figure 1:
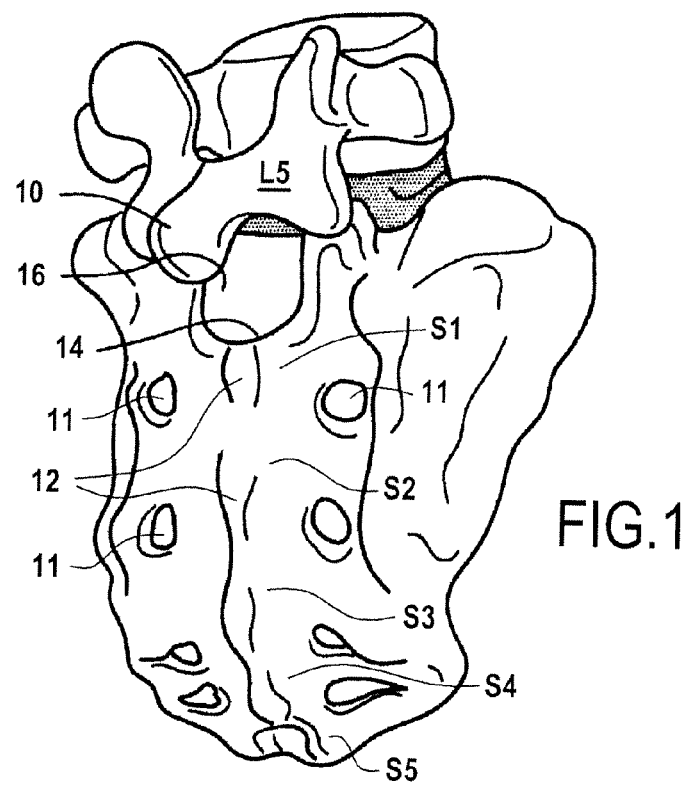
FIG. 1 is a diagram showing the anatomy of the lumbosacral region of the spine.

The fifth lumbar vertebra L5 and the top vertebra S1 of the sacrum are shown diagrammatically in FIG. 1. In its middle posterior portion, the vertebra L5 presents a spinous process 10. This process 10 is situated in the sagittal plane of the spine.

The top portion of the vertebra S1 forms a posterior arc 14. The inside face of the posterior arc 14 faces the vertebral body of the sacrum, it is concave, and it co-operates with the vertebral body to define an orifice referred to as the vertebral foramen 16 and through which the spinal cord (not shown) passes.

The same exemplary spacer 20 is also used for both of the implant examples shown in FIGS. 2 to 5 and 9.

The spacer 20 is designed to be inserted between the spinous process 10 and the posterior arc 14, and it serves to limit the extent to which the spinous process 10 can approach the posterior arc 14 during extension of the spine. It is made of a biocompatible material, e.g. a biopolymer such as polyetheretherketone (PEEK).

The directions up, down, front, rear, right, and left are defined below with reference to the positioning of the spacer on the spine, the front face of the spacer being directed towards the belly of the individual wearing the spacer. The midplane M of the spacer 20 corresponds substantially to the sagittal plane of the spine when the spacer is in place, it intersects the top, bottom, anterior, and posterior faces 22, 24, 26, and 28 of the spacer.

A groove 30 extending along the midplane M of the spacer is formed in the top face 22 of the spacer 20 to receive the spinous process 10 of the vertebra L5. The groove 30 opens out into the anterior and posterior faces 26 and 28 of the spacer.

Furthermore, a longitudinal housing 36 extending orthogonally relative to said groove 30 is provided in the bottom face 24 of the spacer in order to receive the top portion of the vertebra S1. The spacer 20 can thus rest directly on the vertebra S1.

The spacer 20 presents two extensions 32 at its bottom end extending the posterior face 28 thereof. The spacer 20 also includes a tab 34 extending its anterior face 26 and facing the space that is left between the extensions 32. Between them, the tab 34 and the extensions 32 define the above-mentioned longitudinal housing 36. The extensions 32 are spaced apart so as to be capable of housing between them the residual bump 12 of the vertebra S1.

The implant examples shown also have an attachment for attaching the spacer 20 to the spinous process 10 of the vertebra L5. Advantageously, this attachment comprises a strap 46 secured to the spacer 20 and suitable for being tightened around the spinous process 10 of the vertebra L5 in order to hold said process 10 in the groove 30 formed in the top face 22 of the spacer. One end of the strap 46 is fastened to the spacer 20 on one side of the groove 30, while the other end can be passed through an attaching system 42 that is secured to the spacer 20 and situated on the other side of the groove 30. The attaching system 42 may be releasable.

While the spacer 20 is being put into place, the strap 46 is passed around the spinous process 10 and then passed through the attaching system 42. The system 42 may be self-locking so that once the strap 46 has passed through the system in one direction and has been tightened around the spinous process 10, the system 42 prevents the strap from sliding in the opposite direction.

The spacer 20 also includes a hook 21 formed on its posterior face 28 and described in greater detail below.

Figure 2:
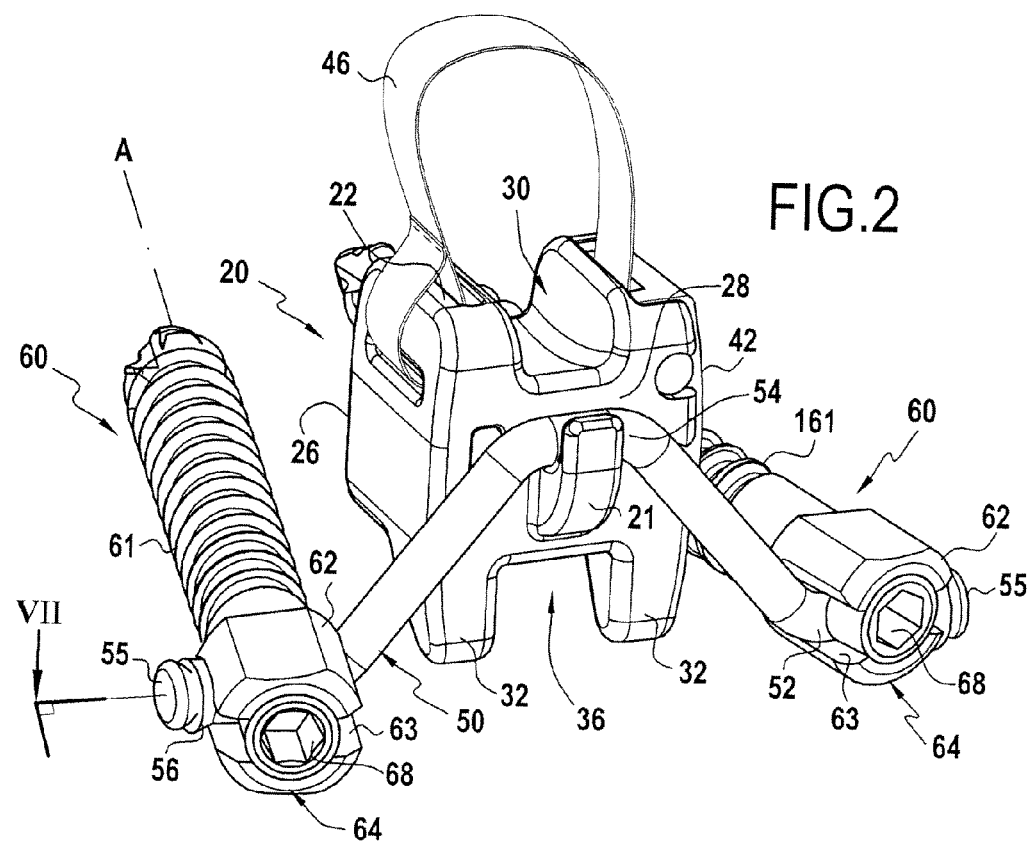
FIG. 2 shows a first example of an implant of the invention.

With reference to FIG. 2, there follows a description of a first example of an implant of the invention.

The implant comprises a spacer 20 of the above-specified type, fitted with an attachment, a flexible tie 50, and two pedicular screws 60 situated on either side of the spacer 20.

Each pedicular screw 60 comprises a screw shank 61 suitable for being screwed into the sacrum, and a screw head 62 suitable for remaining, at least in part, outside the sacrum. This screw head 62 presents a recess 63 25 suitable for receiving an end portion 52 of the flexible tie 50. In this example, the recess is a groove formed in the end face 64 of the screw head. This groove crosses the screw head 62 radially (i.e. orthogonally to the axis A of the screw 60) from one edge to the other. This groove is defined by two opposite side walls 65 and by a bottom wall 66 (see FIG. 6). Between them, in the middle portion of the groove, the side walls define a threaded empty space 67 suitable for co-operating with a clamping screw 68.

The flexible tie 50 preferably presents a certain amount of elasticity. For example, it is made up of at least one tubular braid made from yarns of biocompatible materials such as polyethylene. The braiding, and above all the intrinsic properties of polyethylene ensure that the flexible tie has elasticity. The two end portions 52 of the flexible tie 50 are designed to be fastened to the screw heads 62. Furthermore, an intermediate portion 54 of the flexible tie 20 is suitable for co-operating with a connection system present on the spacer 20. This intermediate portion 54 is preferably substantially in the middle.

In the example, the hook 21 situated at the rear of the spacer 20 provides the connection system. The hook 21 is made integrally with the spacer 20 and projects from the posterior face 28 of the spacer. It faces upwards so as to retain the intermediate portion 54 of the flexible tie 50. Nevertheless, other connection systems could be envisaged, such as a groove formed in the rear of the spacer 20, e.g. in its posterior face 28, or a hole passing through said spacer.

The implant is put into place as follows. Firstly, the screws 60 are fastened to the sacrum. Thereafter, the end portions 52 of the flexible tie 50 are engaged in the recess 63 of the screw heads 62, and the intermediate portion 54 of the flexible tie 50 is engaged in the hook 21. In order to ensure that the end portions 52 of the flexible tie remain in the recesses 63 before being permanently fastened using the clamping screws 68, the flexible tie presents projections 55 at its ends that are of dimensions greater than the width of the recess 63. In addition, washers 56 can be provided between the projections 55 and the screw heads 62. Finally, each end portion 52 of the flexible tie is fastened to its respective screw head 62 by tightening the corresponding clamping screw 68. This screw presses the flexible tie against the bottom wall 66 of the recess 63 in order to hold it in position (see FIG. 6). In order to avoid damaging the flexible tie 50 and avoid any risk of cutting it, the front end of the clamping screw 68 may be rounded.

The tension in the flexible tie 50 can be adjusted by pulling on the end portions 52 of the flexible tie in order to move them away from the spacer 20, prior to fastening them permanently with the help of the clamping screws 68 within the recesses 63.

Once under tension, the flexible tie 50 exerts return forces on the spacer, which forces have a resultant that is directed towards the vertebra S1. In order to ensure that this resultant has a downwardly-directed vertical component of sufficient magnitude, it is preferable for the screw heads 62 to be situated far enough below the hook 21. In addition, precautions can be taken to ensure that the intermediate portion 54 of the flexible tie 50 is situated further back than the end portions 52 of the flexible tie (i.e. rearward relative to the screw heads 62). This enables the resultant of the return forces to have a horizontal component that is directed towards the spine (i.e. towards the front of the spacer 20). Such a horizontal component prevents the spacer 20 from escaping rearwards from the intervertebral space L5-S1.

With reference to FIGS. 3 to 6, there follows a description of a second example of an implant of the invention. The spacer 20 and its attachment, and also the flexible tie 50, are identical to those of the first example. The difference between the two examples lies in the system for holding the end portions 52 of the flexible tie. The second implant example as shown comprises firstly two pedicular screws 160 with respective screw shanks 161 and screw heads 162, and secondly two fastening systems 80 that are distinct from the screw heads 162. Each fastening system comprises a body portion 82. This body portion 82 presents a recess 83 of groove type formed in its front face and within which the flexible tie 50 can be engaged. A clamping screw 88 is suitable for being screwed into a threaded portion of the recess that clamps the flexible tie to the inside thereof and prevents it from moving. In addition, each body portion 82 is extended by a rod 84.

Figure 7:
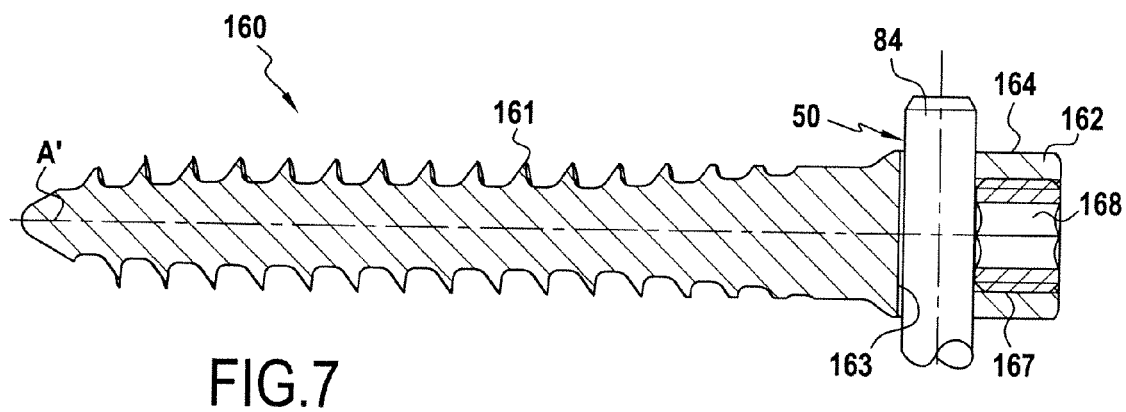
FIG. 7 is an axial section of a pedicular screw head used in the implant of FIGS. 3 to 5.

Furthermore, as shown in FIG. 7, each screw head 162 presents a recess 163, e.g. a hole passing through the screw head perpendicularly to its axis A'. This recess 163 is suitable for receiving said rod 84. The rod 84 can then be fastened to the inside of the recess 163 with the help of a clamping screw 168 co-operating with a threaded hole 167 formed on the axis A' and opening out into the recess 163, so that the clamping screw 168 is suitable for clamping the rod 84 in the recess 163.

By causing the rod 84 to slide in the recess 163, this second implant example makes it possible to adjust the tension in the flexible tie 50. Thus, while the implant is being put into place, it is possible to begin by fastening the intermediate portion 54 of the flexible tie to the spacer 20, and the end portions 52 of the flexible tie to the fastening systems 80, by performing an initial tension adjustment on the flexible tie and then fastening the rods 84 in their final positions so as to perform a second adjustment on the tension of the flexible tie, where necessary.

Figure 8:
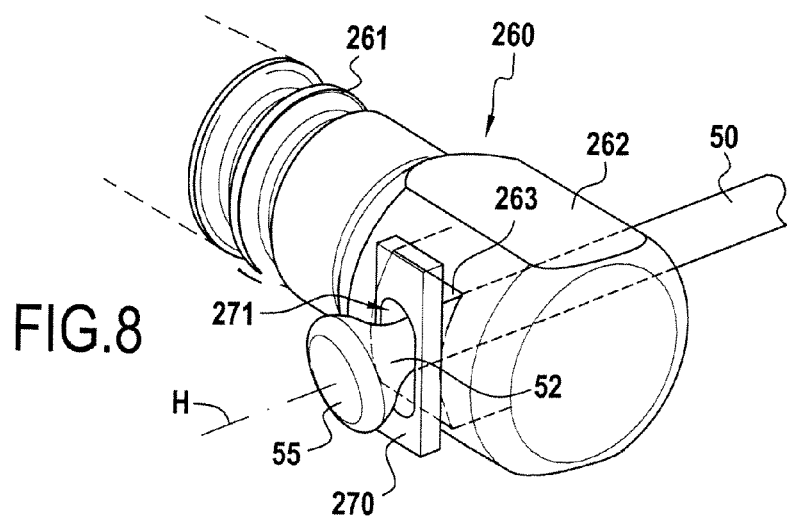
FIG. 8 is an axial section of another example of a pedicular screw head that can be used.

With reference to FIG. 8, there follows a description of another example of fasteners for fastening the end portions 52 of the flexible tie 50 to the sacrum. These fasteners comprise firstly pedicular screws 260 suitable for being anchored in the sacrum and each presenting a threaded screw shank 261 and a screw head 262 pierced by a hole 263, and secondly a pierced plate 270 engaged on the flexible tie 50 and held to the end thereof by a projection 55 present on the flexible tie and formed, for example, by a knot or by a ball of interlaced yarns.

The outline of the hole 263 is such that the plate 270 and the flexible tie 50 can pass through the hole 263 when the plate 270 is inclined substantially along the axis H of the hole, and such that the same plate 270 cannot pass through the hole 263 when it is substantially perpendicular to the axis 8. The plate 270 and the outline of the hole 263 both present a rectangular shape, with the width of the plate being less than the width of the outline of the hole, while the length of the plate is greater than the diagonal of the outline of the hole. In this example, the plate 270 needs to be inclined in the long direction in order to pass through the hole 263.

In order to fasten the flexible tie 50 to the screw head 262, the plate 270, while inclined along the axis H, is passed through the hole 263 together with the end portion 52 of the flexible tie. Once the hole 263 has been passed through, the plate 270 is tilted into a position perpendicular to the axis H. The plate 270 in any event presents a tendency to return into this perpendicular position naturally. Since the flexible tie 50 is under tension, the plate 270 is pressed against the screw head 262 in its position perpendicular to the axis H, such that the end portion 52 (held by the projection 55 and the plate 270 of the flexible tie 50) can no longer escape from the screw head 262. To make it easier to tilt the plate 270 relative to the flexible tie 50, the hole 271 in which the flexible tie 50 is engaged is of oblong shape.

Figure 6:
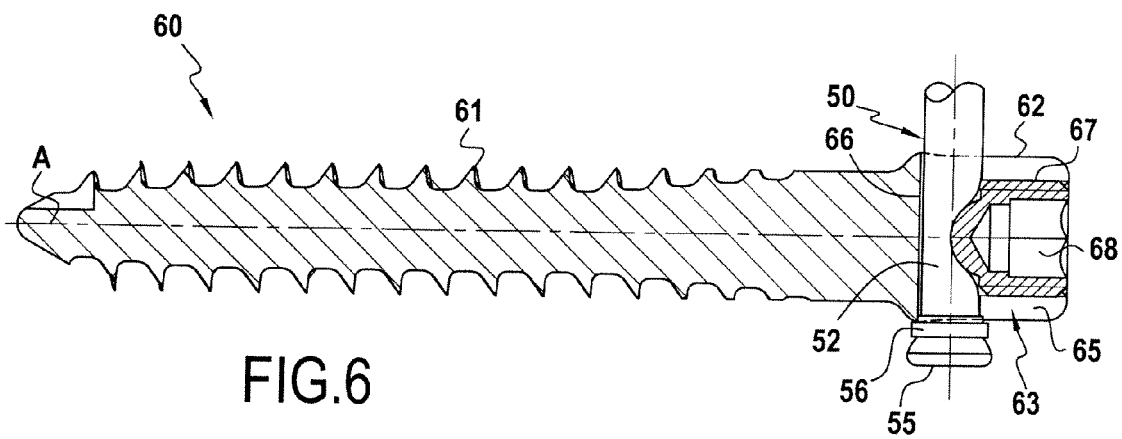
FIG. 6 is an axial section of a pedicular screw head used in the FIG. 2 implant.

Unlike the fastening systems shown in FIGS. 6 and 7, the system of FIG. 8 does not enable the tension of the flexible tie 50 to be adjusted.

Figure 9:
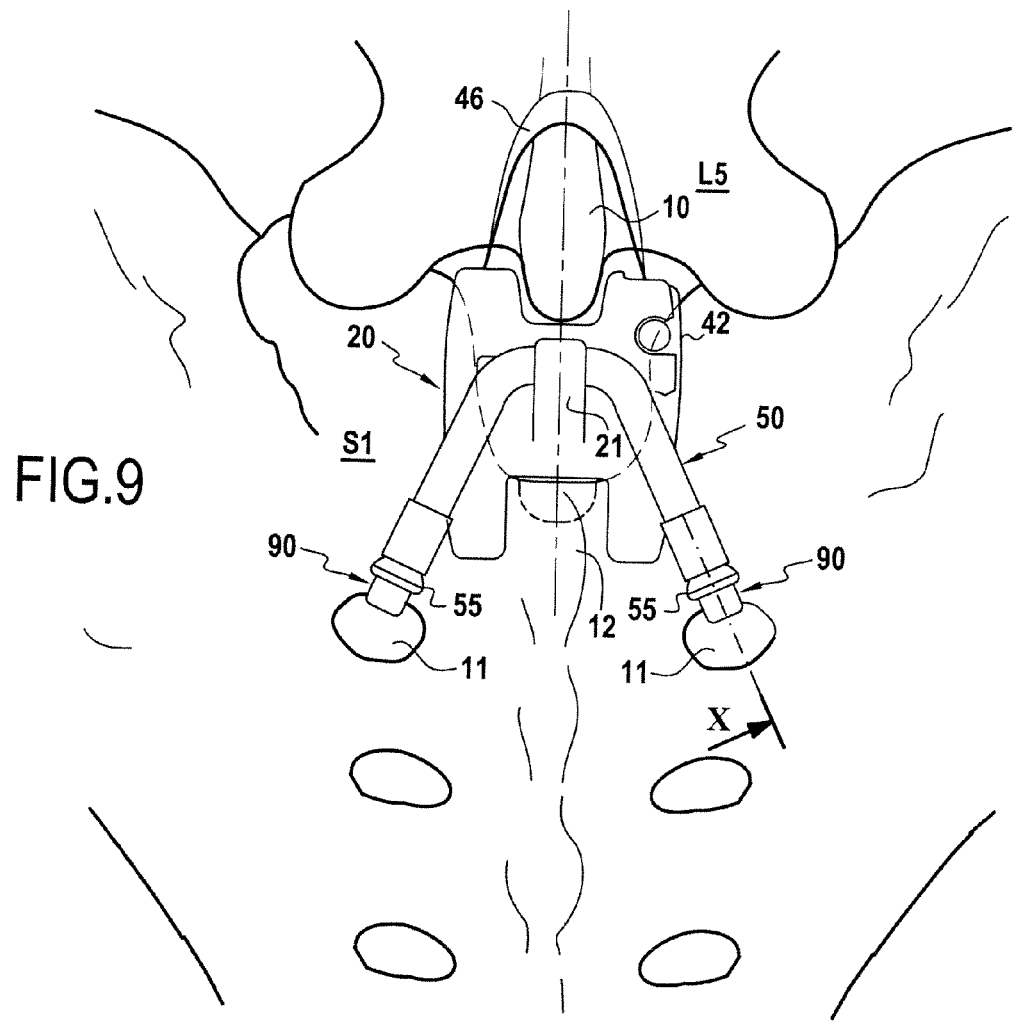
FIG. 9 is a rear view showing a third example of an implant of the invention, put into place between vertebrae L5 and S1.

With reference to FIG. 9, there follows a description of a third example of an implant of the invention. The implant comprises a spacer 20 of the same type as that described above but not including a pedicular screw. Instead of such screws, the implant has hooks 90 suitable for being hooked in the intervertebral foramens 11 of the sacrum, situated under the spacer 20 and on either side thereof. Preferably, one hook 90 is hooked in each of the foramens situated between the vertebrae S1 and S2, i.e. the holes 11 situated closed to the spacer 20.

Figure 10:
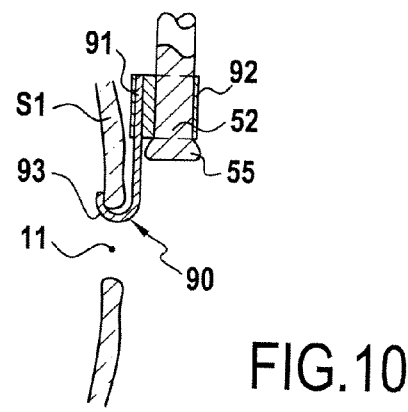
FIG. 10 is a section on plane X showing the flexible tie and the hook of the FIG. 9 implant.

Each end portion 52 of the flexible tie 50 is fastened to a hook by a fastening system. In the example of FIG. 10, the fastening system comprises a sleeve 92 formed on the portion 91 of the hook 90 that is straight (i.e. by opposition to its portion 93 that is curved). The end portion 52 of the flexible tie 50 passes through the sleeve 92 and is retained therein by a projection 55 formed at the end of the flexible tie 50. This projection has dimensions greater than those of the opening in the sleeve 92 so as to be incapable of passing therethrough.

In order to fasten the ends 52 of the flexible tie to the hook 90, it would naturally be possible to envisage using other fastening systems. Thus, it is possible to use systems analogous to those described above and shown in FIGS. 6 to 8, as fitted to the pedicular screw heads, i.e. either a system with a clamping screw co-operating with a recess, or a system with a hole having a special outline co-operating with a plate.

It should be observed that whatever the embodiment used, the flexible tie 50 is put under tension in such a manner as to pull the spacer 20 downwards.

Figure 3:
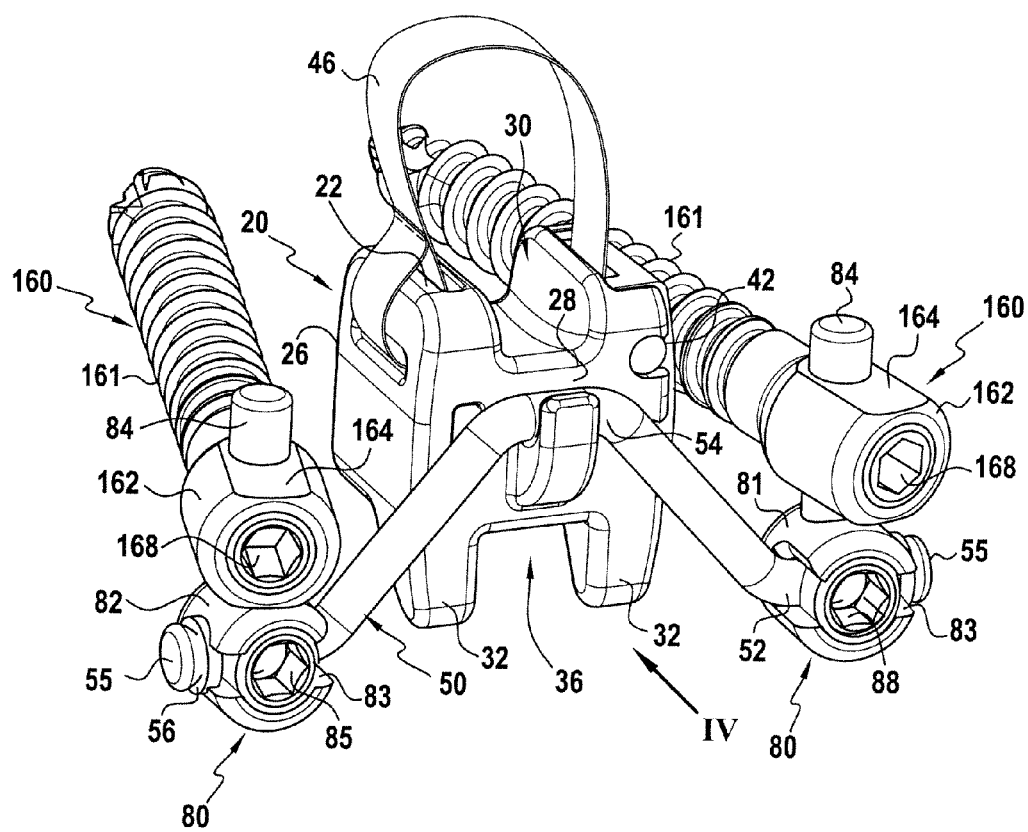
FIG. 3 shows a second example of an implant of the invention.
Figure 4:
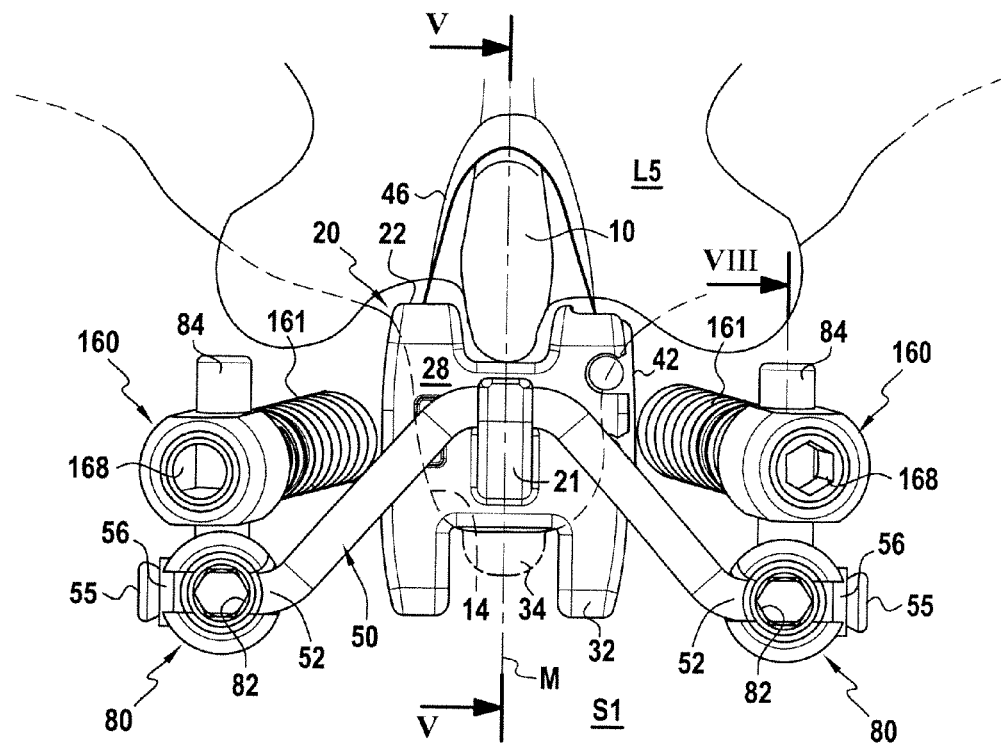
FIG. 4 is a rear view looking along arrow IV showing the FIG. 3 implant once it has been put into place between vertebrae L5 and S1.
Figure 5:
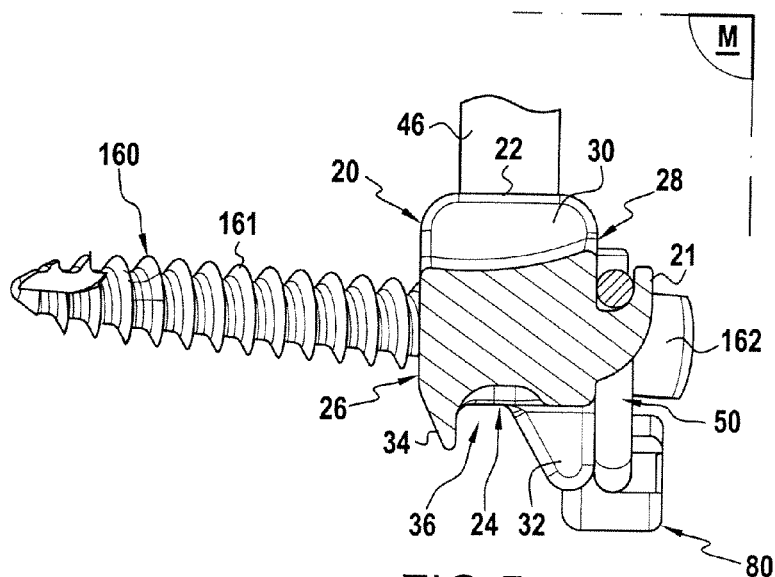
FIG. 5 is a section of the FIG. 4 implant on the midplane M and looking arrows V.

In the embodiments of FIGS. 2 and 3, the end portions 52 of the tie 50 are movable relative to said fasteners and can be pulled away from said spacer 20 to put the flexible tie under tension, prior to being prevented from moving relative to the fasteners.

In the example of FIG. 2, the flexible tie can slide in the recesses 63 in the screw heads 62, prior to being prevented from moving relative thereto by the clamping screw 68.

In the example of FIG. 3, the flexible tie 50 is "doubly" movable. Firstly, it can slide in the recesses 83 of the body portions 82 prior to being prevented from moving relative thereto by means of the clamping screws 88, and secondly the body portions 82 can be moved together with the end portions 52 relative to the heads 162 of the screws 160 fastened to the sacrum.

In the example of FIG. 9, the end portions of the tie 50 may be stationary or movable relative to the hooks 90. When they are stationary, the flexible tie 50 is elastically deformable. The length of the tie 50 is selected in such a manner that when the tie 50 co-operates with the hook 21 of the spacer 20, and when the hooks 90 are in position on the sacrum (as shown in FIG. 9), then the tie 50 is under tension.

The invention claimed is:

1. An intervertebral implant for the lumbo-sacral joint, the intervertebral implant comprising:
   a spacer having:
      a top end comprising a groove for receiving a spinous process of a fifth lumbar vertebra L5, wherein the groove opens out into an anterior face and a posterior face of the spacer;
      a bottom end opposite the top end, the bottom end comprising a longitudinal housing extending orthogonally to the groove;
      at least one extension at the bottom end and extending from the posterior face of the spacer;
      at least one tab at the bottom end and extending from the anterior face of the spacer, wherein the at least one extension and the at least one tab define the longitudinal housing at the bottom end of the spacer; and
      a connection system formed in or on the posterior face of the spacer, wherein the spacer is structured for being placed between the fifth lumbar vertebra L5 and the vertebra S1 of the sacrum that is articulated to the vertebra L5; and
   a flexible tie having:
      end portions attachable to the sacrum via fasteners, wherein said fasteners comprise pedicular screws that are suitable for being anchored in the sacrum, wherein each of the pedicular screws comprises a screw head fitted with a fastening system, and each end portion of the flexible tie being fastened to said screw head via said fastening system; and
      an intermediate portion suitable for co-operating with the connection system of said spacer to connect the spacer to the sacrum.

2. The intervertebral implant for the lumbo-sacral joint according to claim 1, wherein said fastening system comprises a body portion having a recess structured for receiving an end portion of said flexible tie and a clamping screw for clamping the flexible tie inside said recess.

3. The intervertebral implant for the lumbo-sacral joint according to claim 2, wherein the screw head of each pedicular screw forms said body portion of the fastening system.

4. The intervertebral implant for the lumbo-sacral joint according to claim 2, wherein said body portion is extended by a rod, wherein each of the screw heads of the pedicular screws has a respective recess structured for receiving said rod and a clamping screw for fastening said rod inside said recess.

5. The intervertebral implant for the lumbo-sacral joint according to claim 1, further comprising an attachment for attaching said spacer to the spinous process of the vertebra L5.

6. The intervertebral implant for the lumbo-sacral joint according to claim 5, wherein said spacer further comprises a top face at the top end and a bottom face at the bottom end, wherein the groove extends along the midplane of said spacer and is formed in said top face to receive the spinous process of the fifth lumbar vertebra L5, and wherein the longitudinal housing extending orthogonally to said groove is formed in said bottom face to receive the top portion of the vertebra S1.

7. The intervertebral implant for the lumbo-sacral joint according to claim 1, wherein said spacer further comprises a top face at the top end and a bottom face at the bottom end, wherein the groove extends along the midplane of said spacer and is formed in said top face to receive the spinous process of the fifth lumbar vertebra L5, and wherein the longitudinal housing extending orthogonally to said groove is formed in said bottom face to receive the top portion of the vertebra S1.

8. The intervertebral implant for the lumbo-sacral joint according to claim 1, wherein the end portions of the flexible tie are movable relative to said fasteners and able to be pulled away from said spacer to put said flexible tie under tension, and wherein, prior to being prevented from moving relative to said fasteners, the flexible tie exerts return force on said spacer towards said vertebra S1.

9. The intervertebral implant for the lumbo-sacral joint according to claim 1, wherein said connection system comprises a hook formed on said spacer.

10. The intervertebral implant for the lumbo-sacral joint according to claim 1, wherein said spacer further comprises a top face at the top end and a bottom face at the bottom end, wherein the groove extends along the midplane of said spacer and is formed in said top face to receive the spinous process of the fifth lumbar vertebra L5, and wherein the longitudinal housing extending orthogonally to said groove is formed in said bottom face to receive the top portion of the vertebra S1.

11. The intervertebral implant for the lumbo-sacral joint according to claim 1, further comprising an attachment for attaching said spacer to the spinous process of the vertebra L5.

12. An intervertebral implant for the lumbo-sacral joint, the intervertebral implant comprising:
   a spacer having:
      a top end comprising a groove for receiving a spinous process of a fifth lumbar vertebra L5, wherein the groove opens out into an anterior face and a posterior face of the spacer;

a bottom end opposite the top end, the bottom end comprising a longitudinal housing extending orthogonally to the groove;

at least one extension at the bottom end and extending from the posterior face of the spacer;

at least one tab at the bottom end and extending from the anterior face of the spacer, wherein the at least one extension and the at least one tab define the longitudinal housing at the bottom end of the spacer; and a connection system formed in or on the posterior face of the spacer, wherein the spacer is structured for being placed between the fifth lumbar vertebra L5 and the vertebra S1 of the sacrum that is articulated to the vertebra L5; and a flexible tie having;

end portions attachable to the sacrum via fasteners, wherein said fasteners comprise hooks for engaging the intervertebral foramens for the sacrum, and wherein each end portion of the flexible tie is attachable to one of said hooks; and an intermediate portion suitable for co-operating with the connection system of said spacer to connect the spacer to the sacrum.

13. The intervertebral implant for the lumbo-sacral joint according to claim 12, wherein said connection system comprises a hook formed on said spacer.

14. The intervertebral implant for the lumbo-sacral joint according to claim 13, wherein said spacer further comprises a top face at the top end and a bottom face at the bottom end, wherein the groove extends along the midplane of said spacer and is formed in said top face to receive the spinous process of the fifth lumbar vertebra L5, and wherein the longitudinal housing extending orthogonally to said groove is formed in said bottom face to receive the top portion of the vertebra S1.

15. The intervertebral implant for the lumbo-sacral joint according to claim 14, further comprising an attachment for attaching said spacer to the spinous process of the vertebra L5.

16. The intervertebral implant for the lumbo-sacral joint according to claim 13, further comprising an attachment for attaching said spacer to the spinous process of the vertebra L5.

17. The intervertebral implant for the lumbo-sacral joint according to claim 12, wherein said spacer further comprises a top face at the top end and a bottom face at the bottom end, wherein the groove extends along the midplane of said spacer and is formed in said top face to receive the spinous process of the fifth lumbar vertebra L5, and wherein the longitudinal housing extending orthogonally to said groove is formed in said bottom face to receive the top portion of the vertebra S1.

18. The intervertebral implant for the lumbo-sacral joint according to claim 12, further comprising an attachment for attaching said spacer to the spinous process of the vertebra L5.

* * * * *